(12) United States Patent
Li

(10) Patent No.: US 6,759,662 B1
(45) Date of Patent: Jul. 6, 2004

(54) OPTICAL DETECTION SYSTEM

(75) Inventor: Sam Fong Yau Li, Singapore (SG)

(73) Assignee: CE Resources Pte. Ltd., Singapore (SG)

( * ) Notice: Subject to any disclaimer, the term of this patent is extended or adjusted under 35 U.S.C. 154(b) by 0 days.

(21) Appl. No.: 09/744,626

(22) PCT Filed: Jul. 16, 1999

(86) PCT No.: PCT/SG99/00081

§ 371 (c)(1),
(2), (4) Date: Jan. 26, 2001

(87) PCT Pub. No.: WO00/06996

PCT Pub. Date: Feb. 10, 2000

(30) Foreign Application Priority Data

Jul. 28, 1998 (SG) .......................................... 9802727

(51) Int. Cl.[7] ................................................ G01T 1/10
(52) U.S. Cl. .................................... 250/458.1; 356/213
(58) Field of Search ...................... 250/458.1; 356/213, 356/445, 455, 246, 72; 435/6, 173.9

(56) References Cited

U.S. PATENT DOCUMENTS

| | | | | |
|---|---|---|---|---|
| 4,673,657 A | * | 6/1987 | Christian | ..................... 436/501 |
| 4,990,250 A | * | 2/1991 | Hellinger | .................. 210/198.2 |
| 5,483,075 A | * | 1/1996 | Smith et al. | .............. 250/458.1 |
| 5,978,095 A | * | 11/1999 | Tanaami | ...................... 356/445 |
| 5,981,956 A | * | 11/1999 | Stern | ........................ 250/458.1 |
| 6,406,845 B1 | * | 6/2002 | Walt et al. | ...................... 435/6 |
| 2002/0009744 A1 | * | 1/2002 | Bogdanov | ....................... 435/6 |

* cited by examiner

*Primary Examiner*—David Porta
*Assistant Examiner*—Christine Sung

(57) ABSTRACT

An optical detection system comprising an electromagnetic radiation source, a source radiation focusing and collimating means, a photodetector, an emitted radiation focusing means and a source radiation blocking panel. The radiation source is used to direct source radiation onto a sample which is disposed in a sample platform. The source radiation focusing and collimating means is disposed between the radiation source and the sample for focusing and collimating the source radiation onto the sample. The photodetector is adapted for receiving radiation emitted from the sample which has been focused by the emitted radiation focusing means. The source radiation blocking panel, disposed between the source radiation focusing and collimating means and the sample, is unique in that it is capable of reducing light scattering and interference, such that a clear signal from each individual sample can be obtained by the photodetector.

40 Claims, 6 Drawing Sheets

OPTICAL DETECTION SYSTEM

FIELD OF THE INVENTION

The present invention is related to optical detection systems. In particular, the present invention is related to optical detection systems which can analyze multiple samples simultaneously.

BACKGROUND OF THE INVENTION

On many occasions, in chemistry and biology, large numbers of samples need to be analyzed. Particularly in molecular biology, in the Human Genome Project, high speed analyses with high throughput are necessary to achieve the goals of the project. Genetic mapping and DNA sequencing on slab gels are currently performed by using automated DNA sequencing with mono-colour or multi-color fluorescent dye labeling. Because capillary electrophoresis (CE) and particularly CE combined with laser induced fluorescence (CE-LIF) offers rapid charged species analyte separation and high detection sensitivity, it is particularly attractive as a separation technique in DNA sequencing applications. However, the number of capillaries that can be analyzed at one time limits the total throughput of the analysis. To increase the throughput a technique called capillary array electrophoresis (CAE) has been introduced. In this technique multiple capillaries are used in parallel with some advantages over slab gels with multiple lanes. There is a substantial reduction on Joule heating effect. Therefore, higher electric fields can be applied and faster analysis can be obtained. The cost of material is reduced in terms of gel usage due to the reduced diameter of the capillaries, as well as samples usage due to a smaller sample size. Another advantage is the possibility to increase the sample throughput by increasing the number of channels in theory up to thousands, while the slab gels impose physical size and sample loading difficulties.

Various methods for acquiring signals from multiple channels have been described; however, the simultaneous detection of the different channels in CAE still presents some problems. A multiple capillary electrophoresis laser induced fluorescence detector that utilizes a confocal fluorescence scanner is described in U.S. Pat. Nos. 5,091,652 and 5,274,240. The scanner or computer controlled stage translates the capillary array past the light path of a laser beam and the optical detection system. Since relatively heavy components are being moved problems with misalignments of the capillaries relative to the light source are likely to occur. To avoid problems derived from the movement of bulky components in U.S. Pat. No. 5,675,155, a detection system is described where an excitation laser beam is focused and scanned across the is capillary array by the movement of a mirror which is aligned as well to receive the electromagnetic radiation from the sample. The advantages of these approaches are the use of a small local illumination and detection volumes requiring only modest excitation power for optimal signal to noise ratio. Crosstalk between adjacent capillaries is eliminated since only a single capillary is illuminated at a time. On the other hand, because the data acquisition is sequential, i.e., the scan modes are from the first capillary to the last capillary in the array, the use for a very large number of capillaries is limited by the observation time needed per capillary. Loss of information could happen in case of a large number of capillaries.

Another multiplexed detector system for capillary electrophoresis is described in U.S. Pat. No. 5,498,324. The invention involves laser irradiation of the sample in a plurality of capillaries through individual optic fibers inserted into the outflow of each capillary. Quesada and Zhang (Electrophoresis 17, 1841–1851, 1996) improved this design by using fiber optics for illumination and collection of the fluorescent emission orthogonally. One of the advantages of the this approach is that no moving parts are involved. However, in both systems the excitation energy that reaches each capillary does not have a homogeneous distribution and degrades as the numbers of fibers included in the fused taper splitter increases. In addition, detection of the arrays is simultaneous through a CCD combined with microscope or camera lens. Therefore, in this case the limitation of the number of capillaries that can be detected at one time depends on the number of them that can be packed in the imaging field of the detector and the resolution of the detector. The most critical problem in this approach may be cross talk between capillaries because fluorescence from adjacent capillaries can be refracted to reach the detector. Although cross talk between capillaries can be avoided by the use of spacers, it is evident that the use of spacers will reduce the number of capillaries in the array.

A greater number of capillaries can be measured at the same time (U.S. Pat. No. 5,730,850) by arranging capillaries two-dimensionally in a capillary array sheet and using a simultaneous two-dimensional detector. Employing modified sheath-flow cuvette detection, sensitivity is enhanced by eliminating light interferences. However, the simultaneous illumination of all the capillaries requires a complicated system of mirrors to transmit the light beam through the buffer solution path between the capillary holder and the detection window, which in turn may result in differences in intensity.

Accordingly, it is desirable to provide an economical and high sensitive detection system for multiple sample analysis which is easy to set up and easy to handle where bulky moving parts and complicated alignments are minimized.

OBJECT OF THE INVENTION

It is therefore an object of the present invention to provide a system to overcome the shortcomings as stated above.

It is another object to provide an optical detection system which allows only collimated light to reach the sample to be detected.

It is a further object to provide an embodiment of an optical detection system which can perform simultaneous detection in a plurality of samples with reduced scattering and cross-talk.

SUMMARY OF THE INVENTION

The present invention is an optical detection system comprising an electromagnetic radiation source, a source radiation focusing and collimating means, a photodetector, an emitted radiation focusing means and a source radiation blocking panel. The radiation source is used to direct source radiation onto a sample which is disposed in a sample platform. The source radiation focusing and collimating means is disposed between the radiation source and the sample for focusing and collimating the source radiation onto the sample. The photodetector is adapted for receiving radiation emitted from the sample which has been focused by the emitted radiation focusing means. The source radiation blocking panel, disposed between the source radiation focusing and collimating means and the sample, is unique in that it is capable of reducing light scattering and interference, such that a clear signal from each individual sample can be obtained by the photodetector.

In the most preferred embodiment, the source radiation focusing and collimating means comprises at least one convergent cylindrical rectangular lens and the source radiation blocking panel comprises a light absorbing panel with at least one pinhole. The samples are contained in channels or tubes aligned in parallel. For simplicity, the samples contained in the various channels or tubes are referred to as sample volumes. In one embodiment, the emitted radiation focusing means is a convex lens, while in another embodiment, it is a convergent cylindrical lens together with an emitted radiation blocking panel having pinholes. This panel with pinholes will be referred to simply as pinholes in the following description. The pinholes may be connected to scanning or conveying means to allow movement. The system may be used for the detection of radiation absorbance or for fluorescence, including epi-fluorescence. Static pinholes for reducing interference and moving pinholes for sequentially and repetitively illuminating selected sample volumes from an array of samples. In the cases of no cross talk between samples or when cross talk can be eliminated, static pinholes are used to reduce interference due to scattered light, while moving pinholes can be used to eliminate cross talk between samples by sequentially and selectively illuminating only the sample volumes to be measured at any instant of time. In this embodiment, the system includes a plurality of sample volumes in parallel comprising: an array of channels, capillaries, flow cells, bands or wells; at least one electromagnetic radiation source; at least one convergent rectangular cylindrical lens to focus electromagnetic radiation; at least one set of static pinholes or moving pinholes; a scanner for moving the pinholes; and at least one detector aligned to receive electromagnetic radiation collected from the sample volumes. The pinholes are placed in between the array of samples and the detector and for between the array of samples and the electromagnetic radiation source. For operation of the system using static pinholes, the number of pinholes should match that of the samples in the array. The electromagnetic radiation energy that reaches each sample volume is homogeneously focused and distributed by the convergent rectangular cylindrical lens through the array of pinholes. Emitted electromagnetic radiation from all of the sample volumes is collected and directed to a detector simultaneously. Pinholes are used to prevent scattered electromagnetic radiation from reaching the detector. In operation of the system using moving pinholes, the number of pinholes is less than that of the samples in the array and can be as few as one. Only the electromagnetic radiation energy that can pass through the pinholes can reach selected sample volumes. The scanner for moving the pinholes adjusts the position of the pinholes so that only selected sample volumes are illuminated by the electromagnetic radiation. Emitted electromagnetic radiation from the selected sample volumes is collected and directed to a detector where a signal is generated in response to the interaction of the electromagnetic radiation with the sample. This operation is performed sequentially and repetitively with each sample volume in the array. Moving pinholes are also used to prevent scattered electromagnetic radiation from reaching the detector. Advantageously, the present invention provides two detection systems for multiple sample analysis, which are easy to set up and easy to handle where bulky moving parts and complicated alignments are minimized, and allows the electromagnetic radiation source to remain on selected sample volumes for a preset period of time. The result is higher sample throughput, improved detection sensitivity and more economical and physically stable detection systems.

In preferred embodiments, the sample is imaged from an array of channels microfabricated in glass, quartz, fused silica or polymeric materials for capillary electrophoresis. In one embodiment, the source radiation is an excitation light, and the the sample in each channel is fluorescent or contains a fluorescent label and is separated on an electrophoretic medium, or the sample is not fluorescent and is separated in a fluorescent electrophoretic medium. The electromagnetic radiation source preferred is a laser but other right sources, mercury lamps, xenon lamps or any other light sources with the appropriated power and wavelength can be used. The source radiation wavelength specific to the sample to be investigated is isolated by interference filter and transmitted axially to the sample. The source radiation is focused linearly by a convergent rectangular cylindrical lens. The focal distance between the lens and the channels is adjusted manually by movement of a translational stage in the x, y and z directions or by an auto-focusing system. In the same direction the fluorescent emission is collected and collimated by the lens through the array of pinholes or by moving pinholes. A long pass filter is selected to block wavelengths below the emission. An array of pinholes or moving pinholes can be used to prevent non-collimated light from reaching the detector.

The present invention provides detection systems with which a plurality of sample volumes can be analyzed. In consequence, this system allows for a significant increase in throughput of batches of samples. Different types of optical detection systems can be used, such as visible, ultraviolet or fluorescent in the preferred embodiments, we will refer to CE-LIF (laser induced fluorescence), because of its higher sensitivity, performed in microfabricated channels. For those skilled in the art, it is well known that the system is equally applicable for capillary electrophoresis in fused silica capillaries, and since this system is provided with a focusing facility, any coplanar, linear and closely distributed samples can be easily incorporated into the field of view and optically analyzed by the detector. In addition, this multi-channel detection system can be used in the analysis of chemicals, such as ions and drugs, or bio-molecules, such as DNA, RNA, proteins, viruses, bacteria and the like by HPLC or other analytical techniques involving the use of capillaries, microchannels, flow cells, bands or wells. In general it can be useful for optical testing of series of homologous samples volumes distributed closely in reservoirs and in the same plane.

DESCRIPTION OF THE INVENTION

Figure 1B:
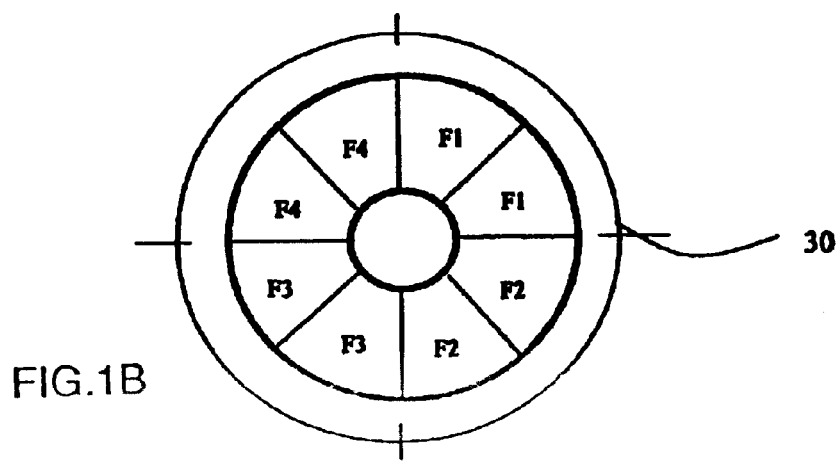
FIG. 1B is a top view of filter wheel shown in FIG. 1A.
Figure 1A:
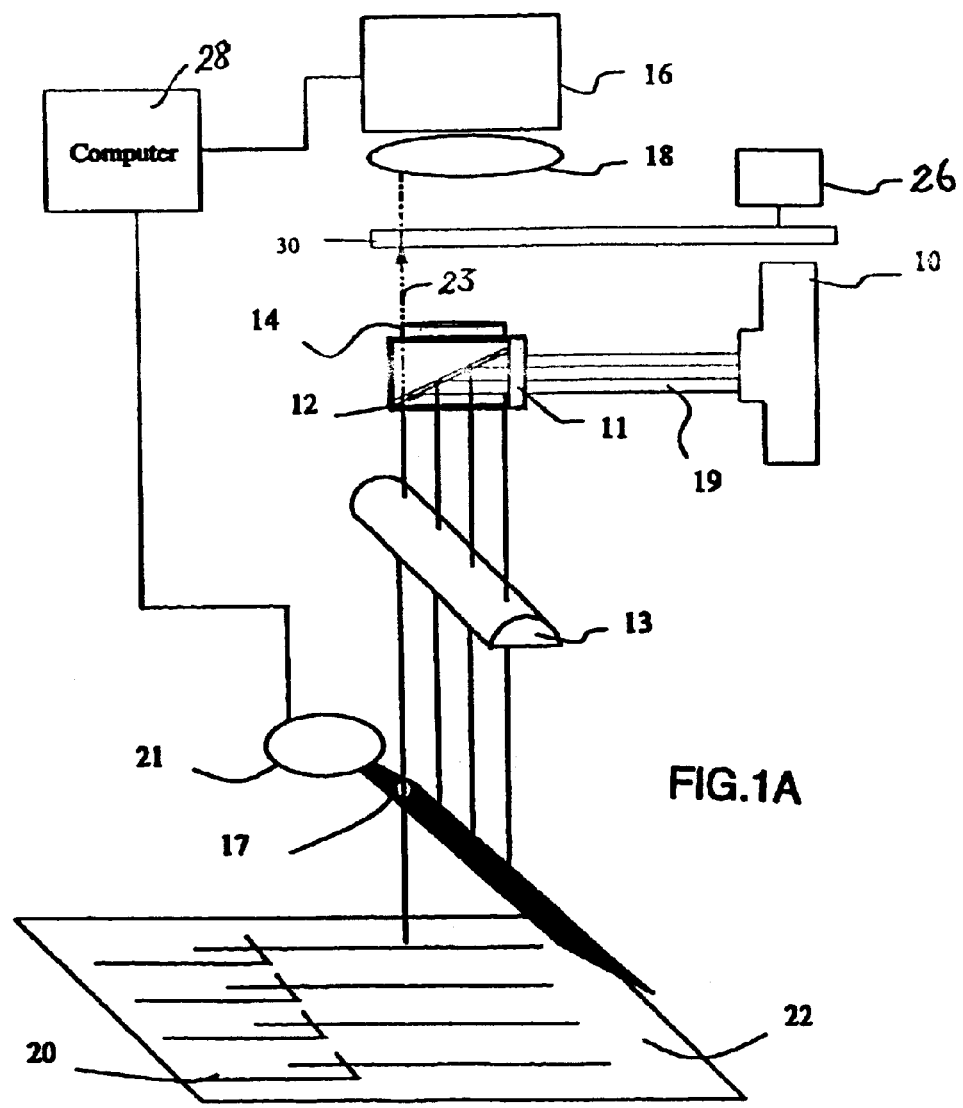
FIG. 1A is a schematic representation of a embodiment of the multichannel detection system in microchip-based capillary electrophoresis utilizing a single moving pinhole for multiple epi-fluorescence detection.

FIG. 1 is a general schematic illustration of the multichannel epifluorescent detection system using a moving pinhole. The system includes a radiation source 10, an interference filter 11, a dichroic beamsplitter 12, a convergent cylindrical rectangular lens 13, a long pass filter 14 and a photon detector 16. The source irradiates excitation light 19 to the dichroic beamsplitter 12 which is positioned at an angle (which is 45°0 in this example) to the beam. This beamsplitter reflects radiation of wavelengths below the specified wavelength, acting as a long pass filter The reflected radiation is then directed axially to the sample channels 20. An interference filter 11 is preferably included in this embodiment to isolate the wavelength necessary for excitation of the fluorescent sample and at the same time eliminate the background scatter caused by the radiation of undesired wavelengths. The interference filter 11 is particularly essential to isolate the necessary excitation wavelength when the light source employed is not monochromatic, such as Hg, Xe, or tungsten lamps. The convergent cylindrical rectangular lens 13 focuses the excitation radiation into a beam of focused light with an elongated cross-section throughout its length, e.g, a line. The axis of the convergent cylindrical rectangular lens 13 is placed perpendicular to the microchannels 20 or, perpendicular to the array of samples to be determined. A single pinhole 17 with an aperture matching the size of the area to be detected allows the excitation beam to reach a selected sample. The resulting fluorescent emission 23 is collected axially by the convergent cylindrical rectangular lens 13, and transmitted through the dichroic beamsplitter 12 and a long pass filter 14, and then focused onto the photodetector 16 by a convex lens 18. The band pass filter 14 is selected to block any background or scattered light from the radiation source. After the release of the emitted radiation 23, a scanner or conveyer system 21 causes the pinhole 17 (not drawn to size) to move to the next microchannel. In this manner, by scanning the pinhole 17, the excitation radiation and the fluorescent emission is sequentially brought to and collected from every microchannel or sample volume in the array. The permanence time of the pinhole in every sample is pre-set and electronically controlled to allow for the excitation and emission of every individual sample before moving to the next. By incorporating a moving pinhole 17, the detection system of the present invention avoids the interference caused by cross talk between channels since one sample is illuminated at the time. By using a pinhole 17, interferences due to scattered light from the optics and the mass of the glass plate 22 comprising the channels are further avoided. The system can be modified for multicolour fluorescence detection by adding a rotating filter wheel 30 (shown in FIG. 1B) before the detector. The filter wheel comprises a predetermined number (usually 4) of band filters which are designed to block the radiation at the wavelengths of the excitation radiation sources and transmit fluorescence at wavelengths typically longer than those for the excitation wavelengths. The filter wheel 30, controlled by means of a rotor 26, rotates and brings sequentially the set of filtered into the path of the emission beam, thus permitting the detection of the fluorescent emission of different dyes present in the sample.

Figure 2:
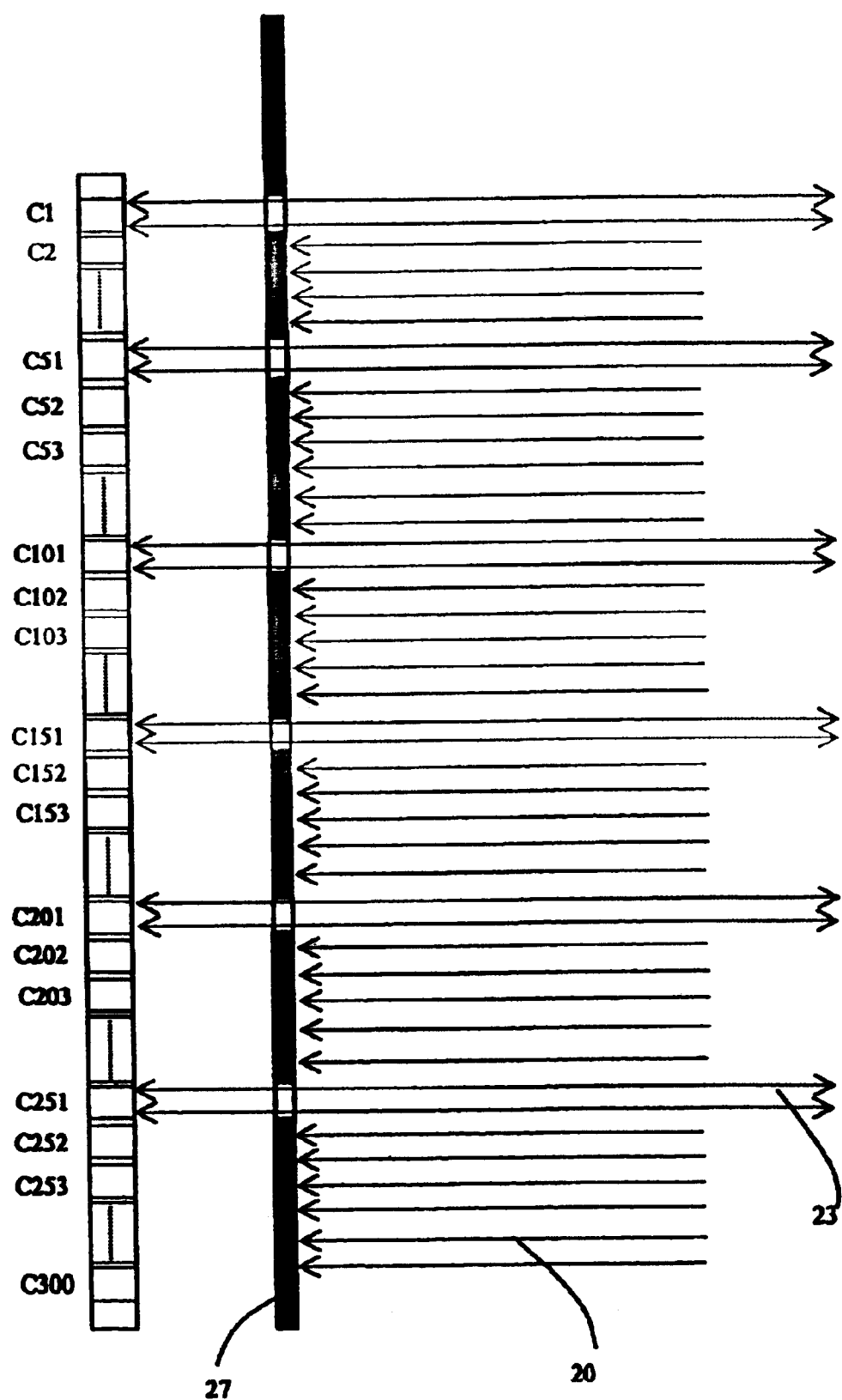
FIG. 2 is the schematic layout of an array of 300 channels scanned simultaneously by 6 pinholes.

Larger number of samples can be monitored by scanning a set of pinholes placed in series provided that the distance between them is large enough to avoid cross-talk between different channels. This situation is depicted in FIG. 2 where 300 microchannels 20 (as numbered as C1–C300) can be scanned by a set of 6 pinholes 27 simultaneously. This approach is advantageous over individual channel scanning since the scanning time per cycle can be decreased. Therefore, the number of channels in the array can be increased. The optical signals collected by the photodetector may be further amplified by an amplifier (not shown in FIG. 1) and analyzed by a computer 28.

Although the preferred embodiment is to irradiate the sample and collect fluorescent emission in the same direction, another possibility is to irradiate the sample and collect fluorescent emission at a different angle. This angle can be varied as long as the excitation radiation 19 does not interfere with the emission radiation 23.

Figure 3B:
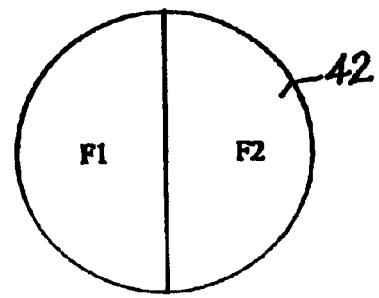
FIG. 3B is top view of the filter wheel shown in FIG. 3A.
Figure 3A:
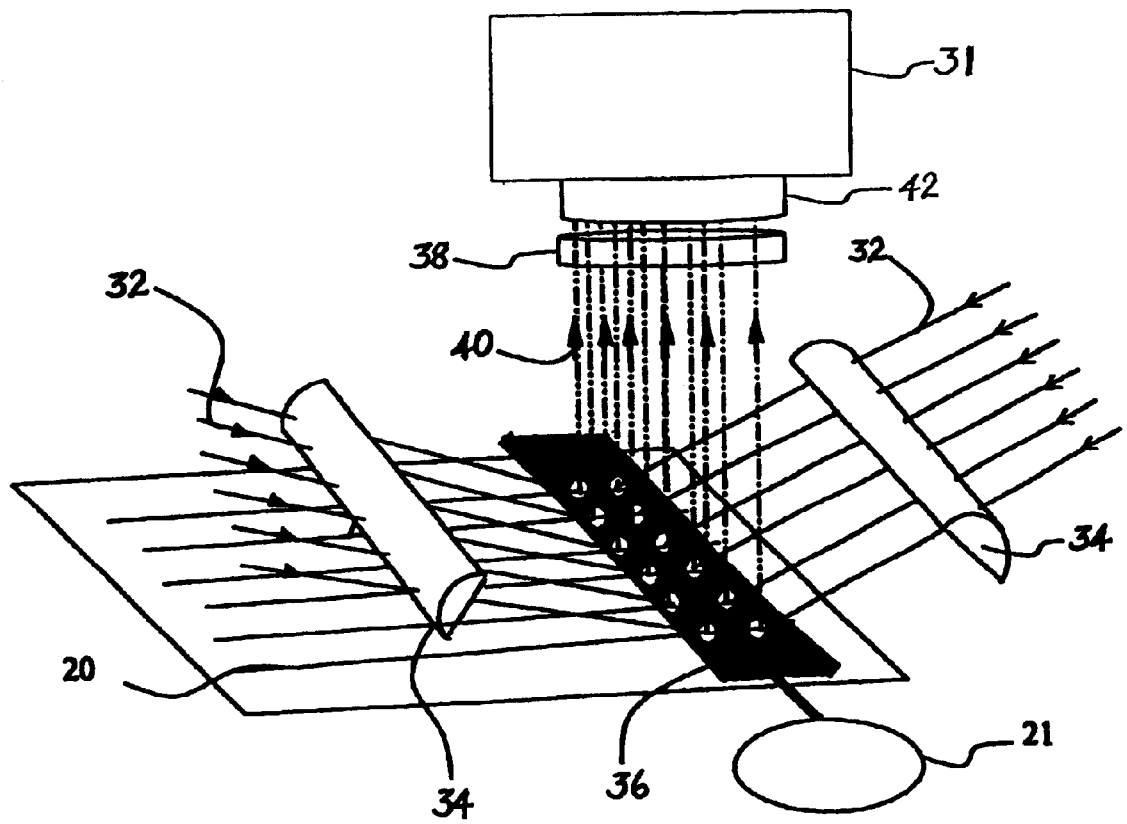
FIG. 3A is the schematic representation of an alternative embodiment of the multichannel detection system utilizing parallel multiple pinholes for multichannel multicolour fluorescence detection imaged on an array detector, e.g. a CCD camera.

FIG. 3A is a schematic diagram of a multi-wavelength fluorescence detection system for multichannel electrophoresis where a detector 31, which may consist of several individual photodetectors, a multi-segmented photodetector or a charged coupled device (CCD) camera is used for detection of two-color fluorescence emission using an array of moving pinholes. The radiation of a laser light source 32 is first split into two color lines and directed at 45° relative to the microchannel plate by two convergent cylindrical rectangular lenses 34. The laser beams are focused on to two different parallel positions. A set of pinhole pairs 36 aligned longitudinally in a parallel array is scanned through the focused beam lines to allow excitation radiation to reach the samples which contain two different fluorescent dyes, the fluorescent emission is allowed to pass through the pinholes 36. If there are more channels than pinholes, the pinholes are moved to a next channel. The fluorescent emission of every dye is captured by the detector 31 through a convex lens 38 at the two different positions simultaneously. To avoid interferences due to fluorescence cross-talk between the two positions of detection, the fluorescent emission 40 of each position is filtered though two band pass filters arranged in parallel in a filter wheel 42 as shown in FIG. 3B. The advantage of using two (or more) laser lines isolated spatially is that a higher duty cycle can be realized compared to the use of filter wheels. With the improved sensitivity and throughput by using an array of moving pinholes, this system can be very useful in analyzing large number of samples.

Figure 4:
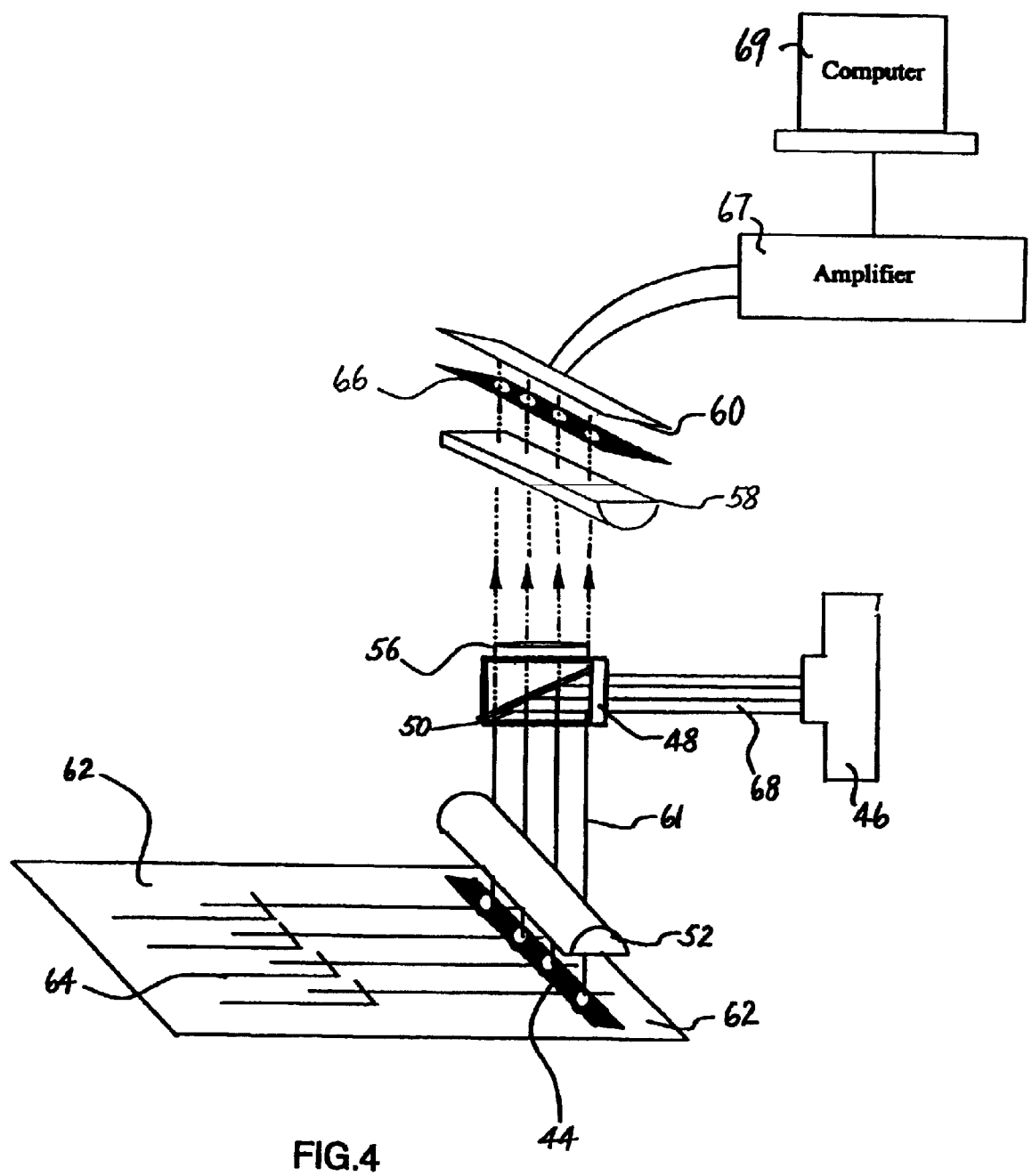
FIG. 4. is the schematic representation of an alternative embodiment of the multichannel detection system utilizing an array of static pinholes for multiple epi-fluorescence detection.

In cases where there is no possibility of cross talk, or when cross talk can be effectively avoided, for example when channels are formed on opague materials, the use of an array of static pinholes is advantageous since no moving parts are involved. FIG. 4 is the general schematic illustration of simultaneous excitation and detection of an array of samples by using an array of static pinholes 44. The system includes a radiation source 46, an interference filter 48, a dichroic beamsplitter 50, a convergent cylindrical rectangular lens 52, an array of pinholes 44, a long pass filter 56, a second convergent cylindrical rectangular lens 58 and a photon detector 60. The emitted fluorescent radiation 61 is collected in the same direction by the first convergent cylindrical rectangular lens 52 and transmitted through the dichroic beamsplitter 50 and a band pass filter 56. A second convergent cylindrical rectangular lens 58 is placed in such direction that it collects, collimates and focuses linearly on to a photo-detector 60 the emitted fluorescent radiation 61 of every sample simultaneously. The array of pinholes 44 with an aperture of the size corresponding to the detection area is placed in front of the channels to avoid interference caused by scattered light from the optics and the mass of the glass plate 62 comprising the channels 64. A second array of pinholes 65 is placed before the photon-detector in order to block any scattered nonparallel light from reaching the detector This signal may then be amplified by an amplifier 67, and analyzed or stored by a computer 69. Since fluorescence is emitted by the sample molecules in all directions, fluorescent refraction from neighboring channels can cause interferences in the detection. To avoid this cross-talk between channels, it is advisable to intercalate a set of blocking channels between pairs of separation channels. The blocking channels may be formed by filling channels with black ink to absorb unwanted fluorescent radiation or reflective materials to reflect radiation.

Although the preferred embodiment is to irradiate the sample and collect fluorescent emission in the same direction, another possibility is to irradiate the sample and collect fluorescent emission at a different angle. This angle can be varied as long as the excitation radiation 68 does not interfere with emission radiation 61.

Figure 5:
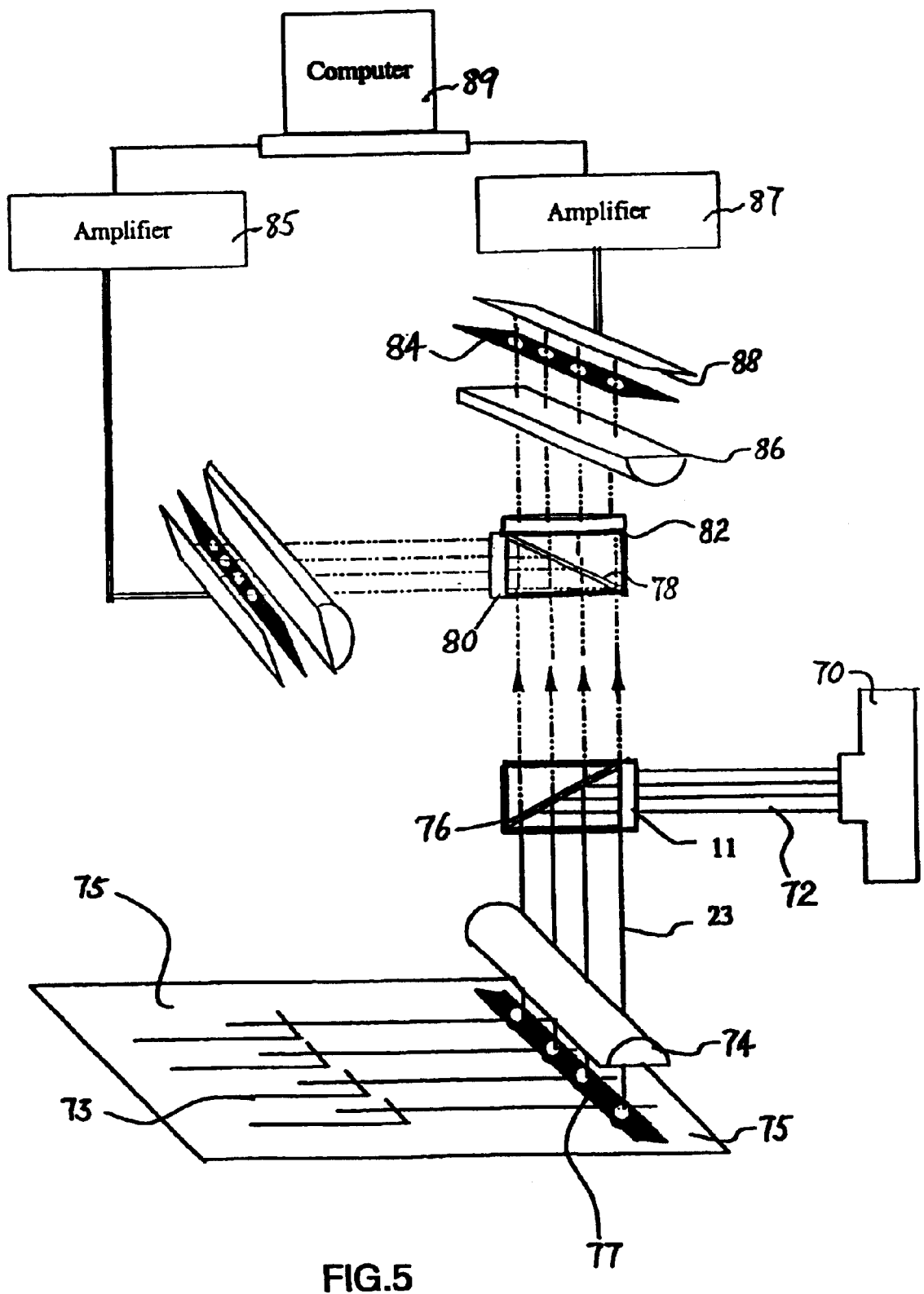
FIG. 5. is the schematic representation of an alternative embodiment of the epi-fluorescence multichannel detection system utilizing an array of static pinholes for multicolour fluorescence detection.

FIG. 5 illustrates a schematic diagram of the multi-detector system with static pinholes suitable for the detection of two different emission wavelengths. This system makes use of a single laser source 70 to generate excitation light 72 of two different wavelengths for two different fluorescent labels. The two different fluorescent labels may be found within each sample inside each sample channel 73 in the sample platform 75. These fluorescent labels should have readily distinguishable fluorescent emissions. During operation, the emission radiation of the fluorescent labels passes through an array of pinholes 77 and is collected by a convergent cylindrical rectangular lens 74, refracted through a dichroic beam splitter 76 and split into two different wavelengths by the use of a second dichroic beam splitter 78. Additional spectral filtering is performed by using a band pass filter 80 for the lower wavelength and a long pass filter 82 for the higher wavelength. The fluorescent signals are then focused through an array of pinholes 84 by convergent cylindrical rectangular lenses 86 on to two photodetectors 88. Again, the signals may be amplified by one or more amplifiers 85 and 87, and the signal analyzed and stored by a computer 89. Those skilled in the art will recognize that a higher number of fluorescent wavelengths can be detected by subsequent division and filtering of the fluorescent emission provided that the appropriated number of labels and excitation radiation wavelengths are used.

Figure 6:
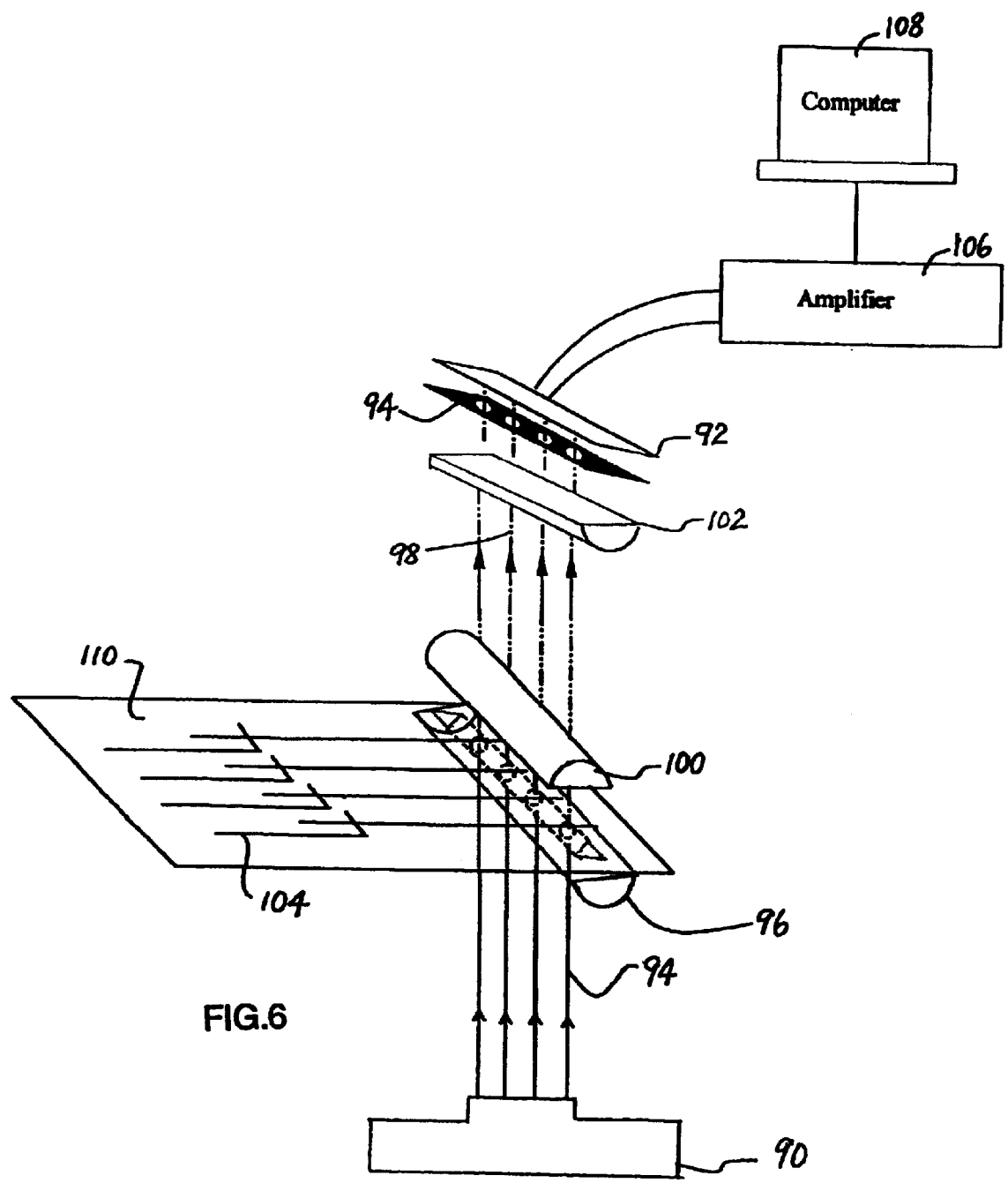
FIG. 6. is a schematic representation of a preferred embodiment of the multichannel detection system in microchip-based capillary electrophoresis utilizing an array of static pinholes for simultaneous absorbance detection.

Another viable application for an array static pinholes is the detection in parallel of the absorbance of an array of samples volumes. As represented in FIG. 6, the radiation source 90 and the photodetector 92 are place in the same plane. The source radiation is electromagnetic radiation, and the emitted radiation is the transmitted radiation which is not absorbed by the sample. Electromagnetic radiation 94 is focused linearly to the array of samples by a convergent cylindrical rectangular lens 96. After the electromagnetic radiation 94 has pass through the sample volumes, the transmitted radiation 98 is collimated by a second convergent cylindrical rectangular lens 100. A third convergent cylindrical rectangular lens 102 focuses on to the photodetector 92 the transmitted radiation. An array of pinholes is placed between the cylindrical lens 96 and the detection volume, allowing a parallel beam of light to pass through the sample. Another array of pinholes 94 is placed in front of the photodetector 92 to avoid scattered light from reaching the detector. As in the other systems, an amplifier 108 may be connected to the photodetector to amplify the signal, The decrease in intensity of the electromagnetic radiation can then be calculated by the electronic components by connecting a computer 108 to the amplifier. This embodiment of the invention is expected to be most useful for detection in high performance liquid chromatography (HPLC), capillary HPLC or microchannel HPLC.

For microchannel separations, the channels 20, 64, 73 and 104 are microchannels which are generated in glass, quartz or fused silica plates 22, 62, 75 and 110 by photolithographic and standard dry or wet-etching techniques. Polymeric materials can also be molded to adopt the desired patterns. Materials which are transparent, physically and chemically stable such as polymethylmethacrylate, polydimethoxysilosane, nylon, polyethylene, polypropylene, fluoropolymers-based polymers and the like can be used as substrate for microfabrication. Microstructures for capillary electrophoresis comprise a channel network that permits dead-volume-free sample introduction and separation. In addition, other procedures such as sample pre-treatment, derivatization, fraction collection etc. can be integrated in the same microstructures. Arrays of microchannels are easily generated in the same structure. Each channel comprises a separation channel and injection channel. Typically, separation channels are straight or serpentine like of 1–100 cm length having a width of 1–100 µm and a height in the order of 1–50 µm, and injection channels intersecting the separation channels. Voltages are applied at the end of the microchannels where buffer and sample reservoirs are located. Flow direction and separation can be controlled by electrokinetic effects due to the harmonic application of voltages in the reservoirs or hydrodynamic effects due to application of pressure or vacuum.

A sample plug introduced into the separation channel is electrophoretically separated along the length of the separation channel. Monitoring of the separated components can be performed at the desired point along the separation channels by focusing the excitation beam and collecting the subsequent fluorescent emission. In this embodiment, the sample platform is a channel plate or a capillary array electrophoresis chip.

A channel plates may be placed in a translational stage to facilitate focusing of the sample volumes on the field of view by the movement of the stage in y, x and z directions. Focusing on the point of detection may be accomplished visually through a rotational trinocular that allows visualization of the channels. This facility is preferred since different microfabricated plates layouts, shapes and sizes can be incorporated and brought into focus. This procedure can be automated if x and z positions are fixed, and focused on the y direction is performed by a manual focusing device or an autofocusing device.

This invention is not limited to the above described details and pictorially accompanying drawings since many changes and modifications may be made to the invention without departing from the spirit and the scope thereof.

What is claimed is:

1. An optical detection system comprising:
   a) at least one electromagnetic radiation source directing source radiation at a sample platform containing at least one sample;
   b) at least one source radiation focusing and collimating means, positioned between the radiation source and the sample for focusing and collimating the directed source radiation into a beam of focused light onto the sample, wherein the beam has an elongated cross-section throughout its length;

c) at least one photodetector adapted for receiving light emitted from the sample;

d) at least one emitted radiation focusing means, positioned between the photodetector and the sample, for focusing the emitted light from the sample onto the photodetector; and e) at least one source radiation blocking panel, positioned between the source radiation focusing and collimating means and the sample, for blocking extraneous radiation of the beam of focused light and the emitted light, said panel having at least one pinhole wherethrough source radiation can pass, said pinhole provided in a position adjacent to the sample such that focused and collimated source radiation is directed onto the sample.

2. An optical detection system according to claim 1 wherein the sample platform comprises at least one microfabricated channel, or a microfabricated array electrophoresis chip, or at least one capillary column, or at least one flow cell.

3. An optical detection system according to claim 1 wherein the sample platform is further connected to a power supply for electrophoresis or chromatography, such that optical detection can be performed concomitantly with electrophoresis or chromatography.

4. An optical detection system according to claim 3 wherein the plurality of channels or columns are longitudinally aligned.

5. An optical detection system according to claim 4 wherein the plurality of channels or columns are longitudinally aligned in parallel along one plane.

6. An optical detection system according to claim 1 wherein the sample platform is further connected to a pressure control system or a flow control system for chromatography, such that optical detection can be performed concomitantly with chromatography.

7. An optical detection system according to claim 1 wherein a dichroic beamsplitter, disposed between the source radiation focusing and collimating means and the photodetector, is provided for reflecting the source radiation onto the sample, and retracting the emitted radiation onto the photodetector;

the photodetector, the emitted radiation focusing means, the dichroic beamsplitter, the source radiation focusing and collimating means and the sample are arranged in a manner such that source radiation is focused onto said sample, and focused emitted radiation is collected by said photodetector;

the source radiation, comprising an excitation radiation, is directed at the dichroic beamsplitter; and a long pass filter is disposed between the dichroic beamsplitter and the emitted radiation focusing means for preventing source radiation from reaching the photodetector, such that epi-fluorescence detection is achieved.

8. An optical detection system according to claim 7 wherein the photodetector, the emitted radiation focusing means, the dichroic beamsplitter, the source radiation focusing and collimating means and the sample are disposed along one plane in this stated order.

9. An optical detection system according to claim 7 further comprising an interference filter provided between the dichroic beamsplitter and the radiation source for isolating a pre-set excitation wavelength.

10. An optical detection system according to claim 7 further comprising a rotatable filter wheel controlled by a rotor, said filter wheel, positioned between the photodetector and the long pass filter, for the transmission of emitted radiation of selected wavelengths from the sample to the photodetector.

11. An optical detection system according to claim 7 further comprising a second dichroic beamsplitter, disposed between the dichroic beamsplitter and the long pass filter, for splitting the emitted radiation into a first wavelength radiation and a second higher wavelength radiation, such that said first wavelength radiation is reflected, and said second higher wavelength radiation is refracted to said long pass filler;

a second photodetector provided for receiving said first wavelength radiation reflected by said second dichroic beamsplitter; and a second emitted radiation focusing means disposed between the second photodetector and the second dichroic beamsplitter for focusing said fist wavelength radiation onto said second photodetector.

12. An optical detection system according to claim 11 further comprising an interference filter disposed between the dichroic beamsplitter and the radiation source for isolating a pre-set excitation wavelength.

13. An optical detection system according to claim 11 further comprising a second interference filter disposed between the second dichroic beamsplitter and the second photodetector for isolating a pre-set excitation wavelength.

14. An optical detection system according to claim 11 further comprising a second emitted radiation blocking panel with at least one pinhole disposed between the second emitted radiation focusing means and the second photodetector, said pinhole wherethrough collimated second higher wavelength radiation can pass.

15. An optical detection system according to claim 11 further comprising a amplifier connected to said photodetector, and a second amplifier connected to said second photodetector.

16. An optical detection system according to claim 15 further comprising a computer or data processor connected to said amplifier, and a second computer or second data processor connected to said second amplifier.

17. An optical detection system according to claim 1 wherein a plurality of pinholes are disposed on the source radiation blocking panel at predetermined distances, said predetermined distance being the distance or a multiple of the distance between the samples arranged in an array.

18. An optical detection system according to claim 1 wherein a plurality of directing means are provided to reflect, transmit and refract the source radiation at the sample from opposing first and second directions;

at least one pair of first and second pinholes provided on the source radiation blocking panel such that source radiation from the first direction can pass through the first pinhole into the sample, and emitted light is emitted through the first pinhole, and source radiation from the second direction can pass through the second pinhole into the sample, and emitted light is emitted through the second pinhole; and the source radiation focusing and collimating means comprises a first and second convergent cylindrical rectangular lens disposed across the path of the source radiation from said first and second directions respectively for focusing the source radiation onto the first and second pinholes.

19. An optical detection system according to claim 18 wherein the plurality of directing means comprises a set of mirrors which split the source radiation into a first excitation wavelength in the first direction and a second excitation wavelength in the second direction.

20. An optical detection system according to claim 18 wherein the plurality of directing means comprises a set of mirrors disposed at angles such that the first and second directions of radiation are both 45 degrees above the plane of the sample platform.

21. An optical detection system according to claim 18 wherein
the sample platform comprises an array of channels aligned in parallel;
the blocking panel comprises a plurality of pairs of pinholes aligned longitudinally in a parallel array, each pair of pinholes positioned directly above a channel of the sample platform; and
the first and second convergent cylindrical rectangular lens focusing the source radiation from said first and second direction into a first color line and a second color line, said first color line directed at the row of first pinholes and said second color line directed at said row of second pinholes.

22. An optical detection system according to claim 1 wherein the emitted radiation focusing means comprises a convergent cylindrical rectangular lens.

23. An optical detection system according to claim 22 wherein the source radiation blocking panel is provided with a plurality of pinholes.

24. An optical detection system according to claim 22 wherein an interference filter is provided between the dichroic beamsplitter and the radiation source for isolating a pre-set excitation wavelength.

25. An optical detection system according to claim 1 wherein said emitted radiation focusing means comprises
a first and second convergent cylindrical rectangular lens; and
an emitted radiation blocking panel with at least one pinhole;
said first convergent cylindrical rectangular lens proximate said sample platform for collecting radiation emitting from said sample platform and focusing said emitted radiation onto said second convergent cylindrical rectangular lens, said second convergent cylindrical rectangular lens directing said focused light onto said photodetector via said pinhole of said emitted radiation blocking panel.

26. An optical detection system according to claim 25 wherein the emitted radiation is transmitted radiation not absorbed by sample.

27. An optical detection system according to claim 1 wherein the radiation source comprises a laser lamp, mercury lamp, xenon lamp or deuterium lamp.

28. An optical detection system according to claim 1 wherein the photodetector comprises at least one photodiode, a photodiode array, a photomultiplier tube or a charge couple device.

29. An optical detection system according to claim 1 wherein the pinholes are circular, and the diameter of the pinhole range between 1 to 1,000 $\mu$m.

30. An optical detection system according to claim 1 wherein the pinholes are rectangular in shape with the sides of the rectangle within 1 to 1000 $\mu$m.

31. An optical detection system according to claim 1 wherein the emitted radiation focusing means is a convex lens.

32. An optical detection system according to claim 1, wherein the pinhole is movable relative to the source radiation focusing and collimating means and the sample platform.

33. An optical detection system according to claim 1, 7, 17, 21, 24 or 25 wherein the source radiation blocking panel is made of a radiation absorbing material and further comprises a plurality of pinholes which are disposed above each of said samples.

34. An optical detection system according to claim 7, 17, 21, 24 or 25 wherein said source radiation blocking panel is made of radiation absorbing material; and scanning means, connected to said source radiation blocking panel, are provided for shifting the source radiation blocking panel at predetermined distances and predetermined time intervals, said predetermined distance being the distance or a multiple of the distance between the different samples arranged in an array; and said predetermined time interval being the time used to collect emitted radiation from each sample via said pinhole.

35. An optical detection system according to claim 1, 7, 17, 21, 24 or 25 wherein the source radiation focusing and collimating means is a convergent cylindrical rectangular lens.

36. An optical detection system according to claim 1, 7, 17, 21 or 24 wherein the emitted radiation focusing means is a convergent cylindrical rectangular lens.

37. An optical detection system according to claim 1, 17, 21, 24 or 25 wherein a plurality of pinholes are disposed on the source radiation blocking panel at predetermined distances, said predetermined distance being the distance or a multiple of the distance between the samples arranged in an array.

38. An optical detection system according to claim 1, 7, 17, 21 or 24 wherein the source radiation is excitation light and the emitted radiation is fluorescence light.

39. An optical detection system according to any one of claim 1, 7, 17, 21, 24 or 25, wherein the photodetector is connected to an amplifier.

40. An optical detection system according to any one of claims 1, 7, 17, 21, 24 or 25 wherein the photodetector is connected to a computer or a data processor.

* * * * *